United States Patent [19]
Campos

[11] Patent Number: 5,097,833
[45] Date of Patent: Mar. 24, 1992

[54] TRANSCUTANEOUS ELECTRICAL NERVE AND/OR MUSCLE STIMULATOR

[76] Inventor: James M. Campos, 22302 Center St., #2, Castro Valley, Calif. 94546

[21] Appl. No.: 409,121

[22] Filed: Sep. 19, 1989

[51] Int. Cl.⁵ .............................................. A61N 1/36
[52] U.S. Cl. .................................................... 128/421
[58] Field of Search ...................... 128/419 R, 421, 422

[56] References Cited

U.S. PATENT DOCUMENTS

| | | | |
|---|---|---|---|
| 2,350,797 | 9/1941 | Morland et al. | 128/421 |
| 3,946,745 | 3/1976 | Hsiana-Lai et al. | 128/421 |
| 4,121,594 | 10/1978 | Miller et al. | 128/422 |
| 4,338,945 | 7/1982 | Kosugi et al. | 128/421 |
| 4,541,432 | 9/1985 | Molina-Negro et al. | 128/421 |
| 4,640,286 | 2/1987 | Thomson | 128/421 |
| 4,688,574 | 8/1987 | Dufresne et al. | 128/421 |
| 4,690,145 | 9/1987 | Smith et al. | 128/421 |
| 4,919,139 | 4/1990 | Brodard | 128/421 |

OTHER PUBLICATIONS

Mettler Electronics Corp., "Muscle Stimulator User Manual," Jun. 1986.

*Primary Examiner*—William E. Kamm
*Assistant Examiner*—Kennedy J. Schaetzle
*Attorney, Agent, or Firm*—Jensen & Puntigam

[57] ABSTRACT

A transcutaneous muscle/nerve stimulator having a signal generator which produces a train of sine pulses about a zero volt reference line in which the pulses have an alternating order of polarity on a predetermined basis. The amplitude of and width of the positive and negative excursion portions of the pulses, respectively, may be controlled independently for each sine pulse; in addition, the respective positive and negative excursions may be separated by a time delay of selected duration. These features may also be modulated so that they change at a predetermined rate. The signal generator includes a pulse modulation feature which produces an exchange or shifting of selected pulses in the pulse train to produce groupings of two, three, or two plus one pulses or other groupings.

23 Claims, 10 Drawing Sheets

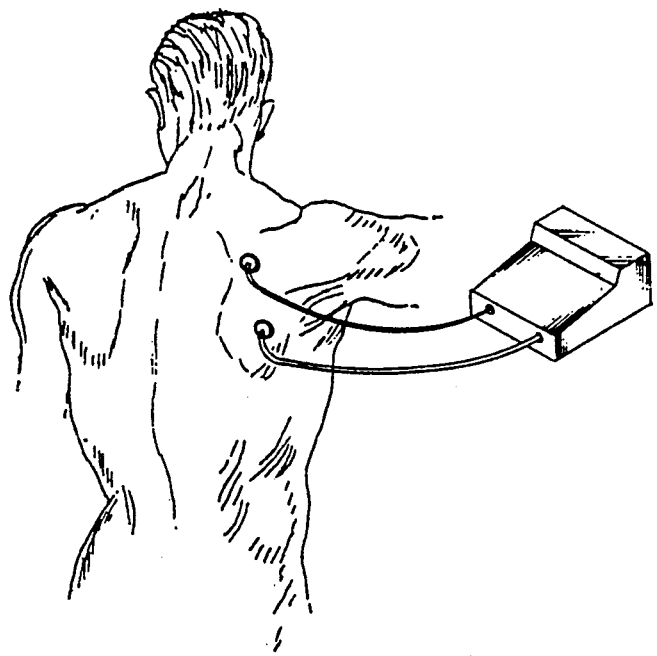
FIG. 1
FIG. 2
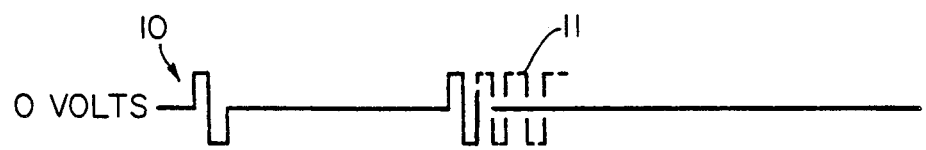
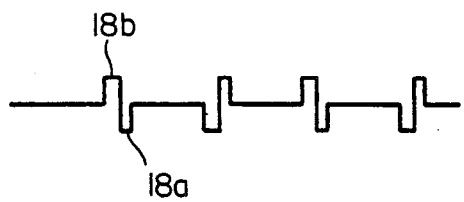
FIG. 4A
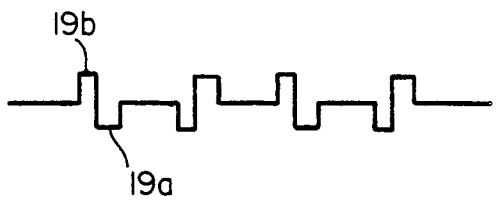
FIG. 4B

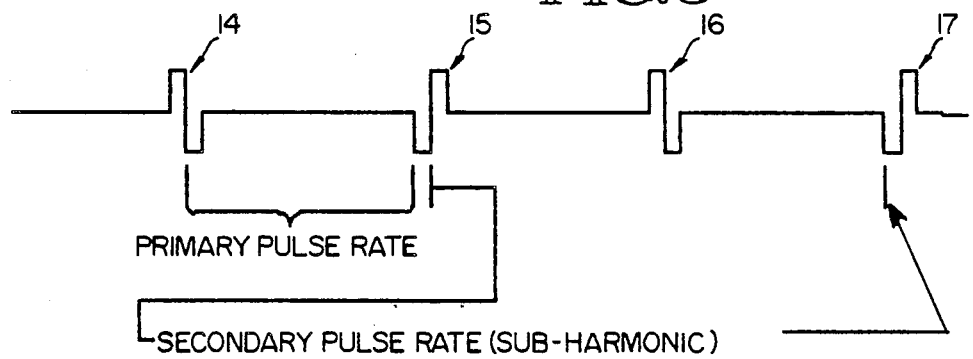
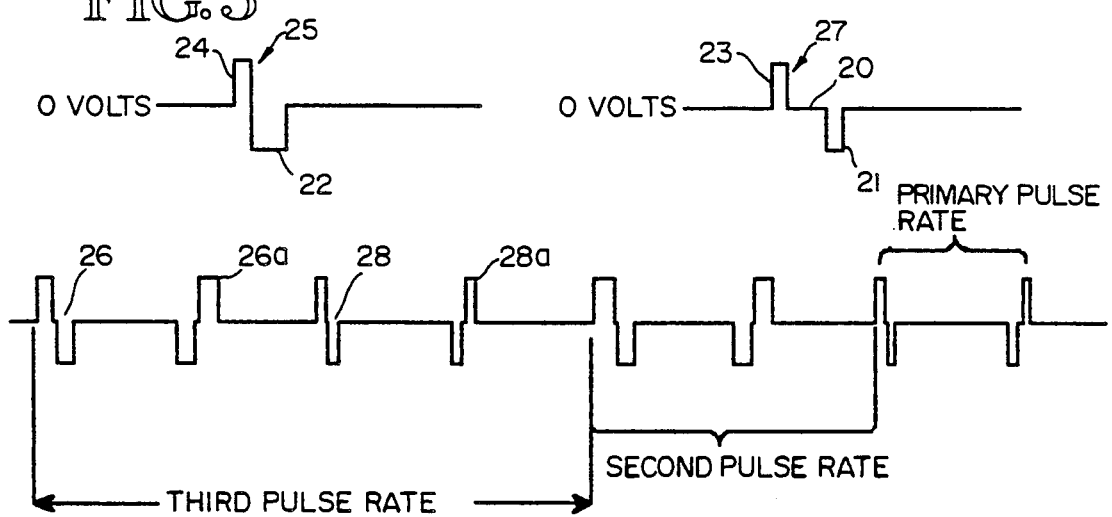

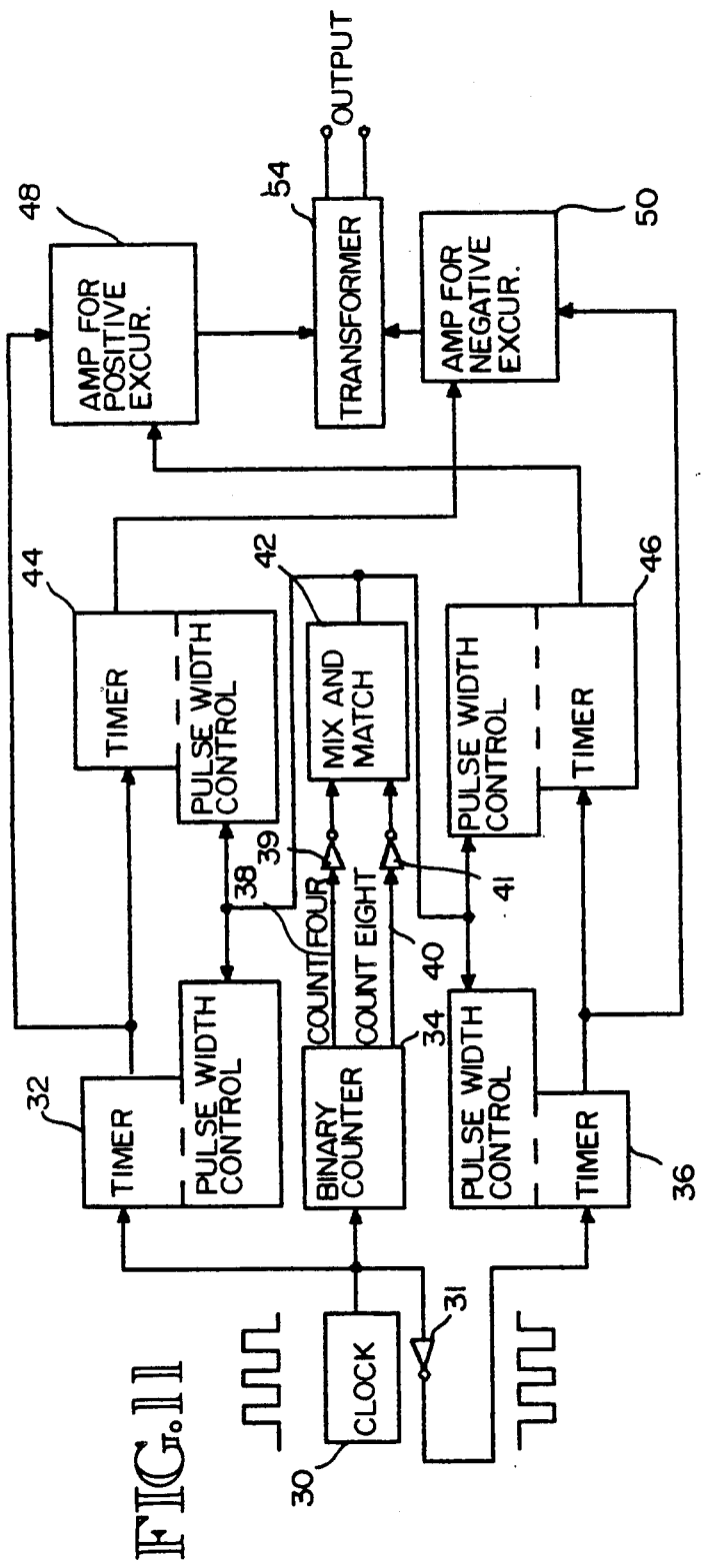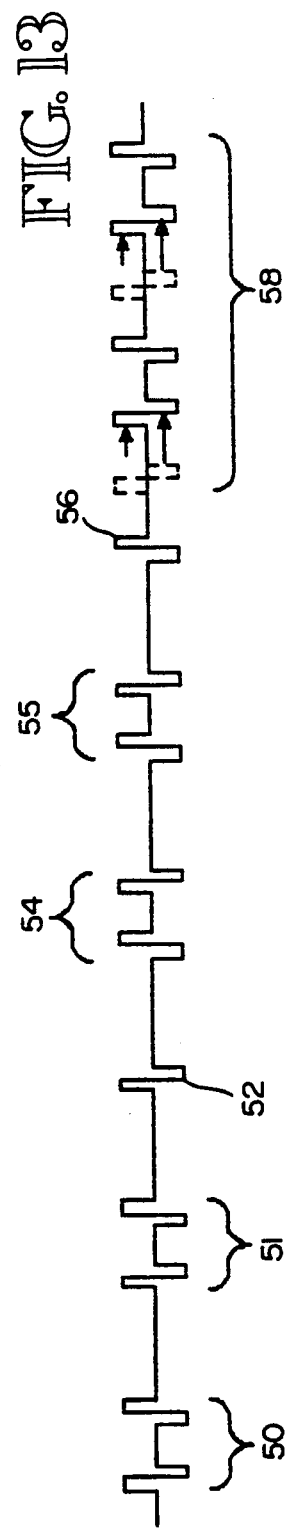

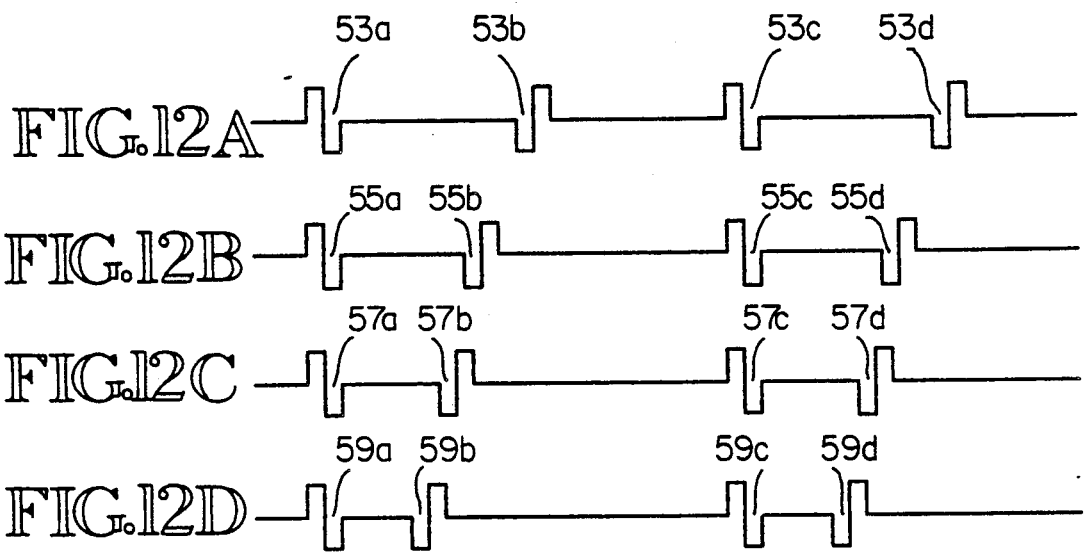
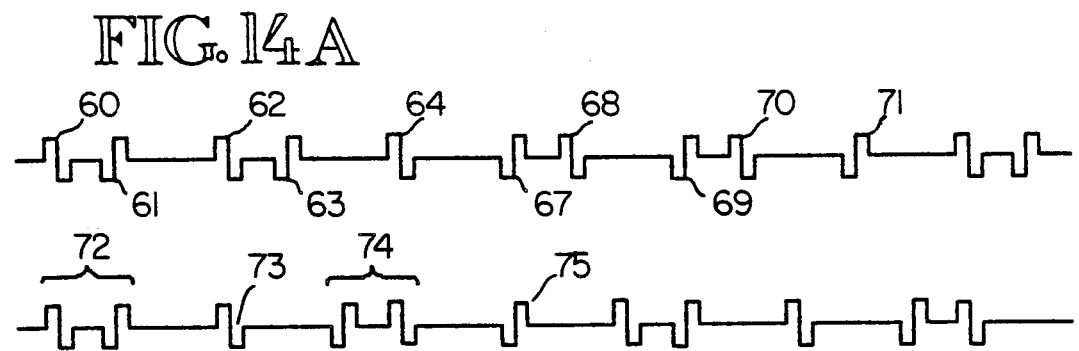

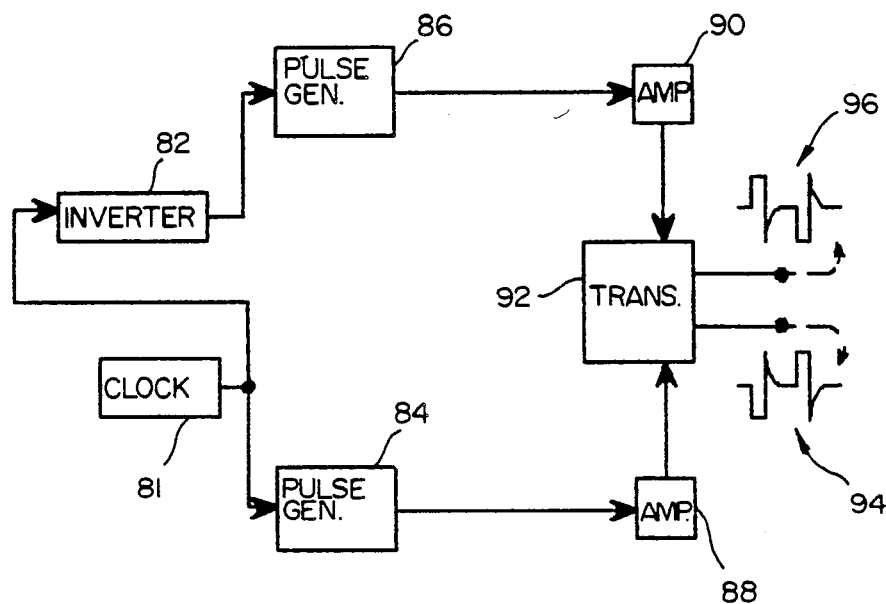
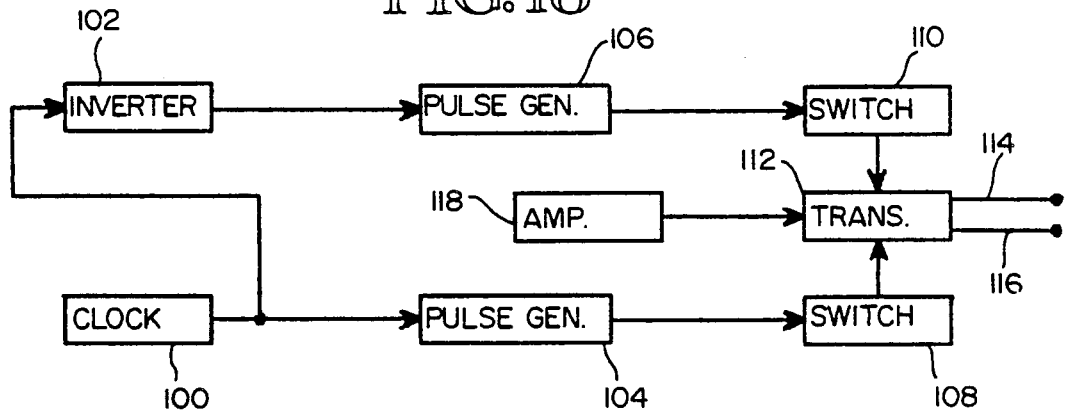

TRANSCUTANEOUS ELECTRICAL NERVE AND/OR MUSCLE STIMULATOR

TECHNICAL FIELD

This invention relates generally to the art of transcutaneous nerve/muscle stimulators and more specifically concerns such an apparatus in which the electrical pulses applied to the nerves and/or muscles are arranged in particular patterns and are so configured to provide a high degree of therapeutic benefit while minimizing discomfort.

BACKGROUND ART

Electrical apparatus for transcutaneously (through the skin) stimulating nerve and/or muscle tissues in the human body are generally well known, heretofore primarily for therapy or to control pain. In therapy for injured muscles, for instance, electrical signals are applied so as to contract and relax the muscle to bring in nutrients and release toxins therefrom, thereby promoting healing of the muscle.

Such electrical apparatus has also been used to maintain or enchance muscle tone, as well as muscle size and strength. Many of these devices use what is referred to hereinafter as a sine wave pulse signal to transmit electrical energy to the bodily area of interest. The term sine wave pulse, as used herein, is a pulse having positive and negative excursions about a zero voltage line. A sine wave pulse may be in the form of a sine wave, as that term is commonly understood, or it may comprise a square wave, or any other configuration, so long as the signal includes successive positive and negative going excursions, or vice versa, centered substantially about a zero volt reference line.

In this category of electrical transcutaneous devices, it is well known to control both the pulse rate, i.e. the rate at which the sine wave pulses occur, as well as the duration or width of each pulse. Both of these parameters may typically be varied within a selected range available on the device itself, particularly in pain control devices which have varying optimal operating conditions, depending upon the user and the level of pain encountered. The device may also have fixed, i.e. nonvariable, values of pulse rate and width in order to provide particular therapeutic results.

In many cases, however, particularly in therapeutic situations, optimum results are not obtained, because the discomfort caused by the electrical signals results in an increase in muscle tension in the body, interfering with the therapeutic process. Heretofore, a significant reduction of optimum therapeutic results must be accepted in order to achieve reasonable or acceptable comfort levels.

The discomfort to the patient is caused by irritation to the skin as well as irritation to the muscle or nerve. Skin irritation is typically due to the electrical resistance of the skin. The skin will readily and typically painlessly pass pulses with therapeutically significant voltage levels having relatively short pulse widths (100 microseconds or less). However, the longer the pulse width, with other factors such as voltage level remaining the same, the more resistive the skin generally tends to act, and skin irritation increases accordingly, producing an unpleasant stinging effect. The effect will vary from patient to patient, depending upon the sensitivity of each patient. Also, at high pulse rates (100-1000 pps), painful tetany is experienced under the electrodes.

Muscle irritation is dependent upon pulse rate and pulse width. Typically, the lower the pulse rate, the farther the contractile effect penetrates into the muscle. Lower pulse rates (4-25 pps) produce a sudden "pulling and dropping" effect in which the muscle contracts too fast or too hard. The longer the pulse width, the more pronounced is the effect.

There is often an imbalance of contractions which is experienced by the user, because the muscle under the one electrode that initially goes positive before transitioning negatively will contract more strongly than the muscle under the electrode that initially goes negative before transitioning positively. This is apparently due to the fact that muscles react to change in the voltage applied and that a negative-going change has a significantly greater effect than a corresponding positive-going change. Hence, the muscles closest to the area of negative stimulus contract more strongly than the muscles closest to the area of positive stimulus. The amount or strength of the stimulus will depend on the overall change in the voltage applied, i.e. from $+25$ v to $-25$ v, rather than the actual level per se of the voltage. Thus, specifically for sine wave pulses, the muscles closest to the area of stimulus receiving a negative-going signal from an initially positive signal level will experience a greater contraction than those muscles closest to the area of stimulus receiving a positive-going signal from an initial negative signal level.

It is also known that an ion transfer phenomenon occurs in tissue when electrical pulses are applied thereto. When the positive-going and negative-going pulses are electrically balanced, a net ion transfer does not occur, but the muscle contraction feels unbalanced, due to the contraction effect discussed immediately above. When the muscle contraction is balanced by unbalancing the positive- and negative-going pulses, the now stronger positive pulse causes an ion transfer which is not fully compensated for by the negative pulse. This net ion transfer can result in discomfort and/or a chemical change in the tissue under the electrodes, effects which are generally regarded as undesirable in sine pulse therapy.

Therefore, in summary, in conventional sine wave therapy, either a contractile imbalance or a net ion transfer occurs.

In another approach, using electrical pulses in a particular manner referred to as DIC (dual inferential currents), the above-described problems with skin irritation and electrical (contractile) imbalance are eliminated. With the DIC approach, four electrodes are used with two high frequency signals. The frequencies of the two signals are slightly different, and where the two signal paths intersect, at the bodily area of treatment interest, there is a nulling effect, and the effective signal frequency at the treatment area is the difference between the frequencies of the two individual signals. The disadvantage of this approach, however, is the cost of the equipment and the set-up time required, as well as the necessity of a trained operator.

The present invention, on the other hand, is directed toward a transcutaneous apparatus which produces a sine pulse train which overcomes the disadvantages of the prior art and produces a high therapeutic effect for selected nerve/muscle tissue with minimal resulting discomfort.

DISCLOSURE OF THE INVENTION

The present invention includes both an apparatus and a method for transcutaneously stimulating nerves and/or muscles in a body, including the generation of an electrical signal which includes a sequence of pulses having positive and negative excursions relative to a reference voltage, and the application of the electrical signal to a selected portion of the body. The sequence of pulses is characterized by various features, including having the pulses change between being initially postive-going and initially negative-going at preselected intervals, separating the positive and negative excursions with a selected time delay, changing the time duration of at least one of the positive and negative excursions, modulating the sequence of pulses to shift individual pulses in time within the sequences, and changing the pulse repetition rate at a predetermined rate which is sufficiently fast that the body perceives the sequence of pulses as including multiple simultaneous frequencies.

BRIEF DESCRIPTION OF THE DRAWINGS

FIG. 1 is a schematic view of the transcutaneous nerve/muscle stimulation apparatus of the present invention, shown in position on a human body.

FIG. 2 is a sine pulse diagram associated with a transcutaneous nerve/muscle stimulator of the prior art.

FIG. 3 is a sine pulse diagram produced by the apparatus of the present invention, illustrating an important feature thereof, namely alternating pulse polarity.

FIGS. 4A and 4B are sine pulse diagrams illustrating additional features of the present invention, namely control over the width of one portion of successive pulses.

FIG. 5 shows sine pulse diagrams illustrating further features of the present invention, including the use of null time.

FIG. 8 is a sine pulse diagram illustrating several pulse rates present in a particular sine pulse train.

FIG. 11 is a block diagram of a circuit for producing the sine pulse diagram and timing diagram shown in FIG. 10.

FIGS. 12A-12D are sine pulse diagrams illustrating various sine pulse pairings which result in a multiple frequency sine pulse train.

FIG. 13 is a sine pulse drawing illustrating several features of the present invention, including the shifting of pulses within the sine pulse train to produce single pulses.

FIGS. 14A-14B are sine wave diagrams illustrating additional features of the present invention.

FIG. 17 is a circuit block diagram of one embodiment of the present invention.

FIG. 18 is a circuit block diagram of an alternative embodiment to that of FIG. 17.

BEST MODE FOR CARRYING OUT THE INVENTION

Figure 6:
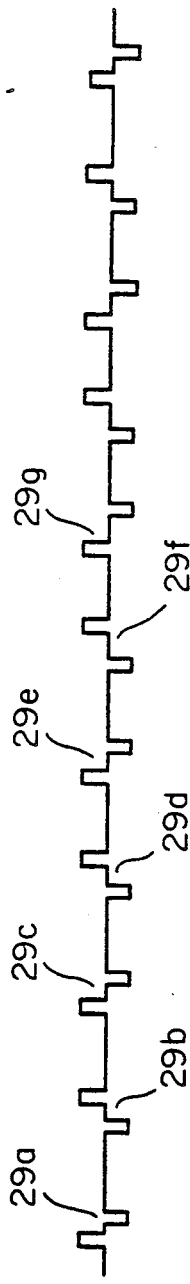
FIG. 6 is a sine pulse diagram illustrating a combination of several features of the present invention, including the feature of null time modulation.

FIG. 2 shows a typical sine pulse train of electrical signals produced by known transcutaneous electrical therapeutic devices. Generally, in such devices, the pulse train is generated by an electrical circuit apparatus and applied through leads to electrodes which are positioned on the specific areas of interest on the human body. Such devices are generally well known and are used for therapy in the treatment of nerve and muscle disorders and injury as well as to control pain associated therewith. It is the electrical signal, i.e. the pulse train, which accomplishes the desired results. The circuit to produce the signal is typically of conventional design, powered by a source of low voltage such as a 9-volt battery.

Basically, the sine pulse train of FIG. 2 includes a successive plurality of sine pulses shown generally at 10, each sine pulse having positive and negative excursions of equal magnitude, about a centerline of zero volts. The time between successive pulses establishes the pulse rate, i.e. frequency, which is usually measured in pulses per second (pps). Typically the time between pulses is substantially greater than the duration of each pulse. Relative to muscle response, such a pulse train has two basic frequencies, one being the actual pulse rate, and the other being a rate extrapolated as if the individual pulses (pulse 10) were a continuous train of pulses, as shown by the dotted lines indicated at 11 in FIG. 2. Both of these basic frequencies are typically variable. However, such a pulse train is limited in its therapeutic effect, as discussed above, by the discomfort caused by the electrical signals and by the imbalance in the muscle contractions.

More specifically, relatively low frequencies in the range of 4-20 pulses per second (pps), produce deep muscle contractions, which generally will produce a uniform contractile effect through the muscle or muscle groups of interest and in turn a high therapeutic and/or muscle building effect. For therapy applications, successive contractions of the muscle caused by the electrical stimulus results in alternately drawing in nutrients to the muscle/nerve tissue via increased blood flow and then forcing the toxins in the muscle out into the blood and away from the muscle. However, in this frequency range, the muscle is easily irritated and the resulting discomfort is quite high.

In a medium frequency range, i.e. 20-75 pps, the therapeutic effect is generally not nearly as great, because the resulting contractions do not go as deeply into the muscle as the contractions for the lower frequencies; however, the pulse train is more comfortable. At a higher frequency range, i.e. 75 pps and above, only relatively shallow muscle contractions are produced, which tend to result in rigid muscle contractions in the immediate area of contact with the electrode. As the frequency increases significantly above that level, i.e. 1,000 pps and above, virtually no muscle contractions are produced.

It is known that voltage change determines contractile effect and that the direction of that change significantly influences the strength of the contraction. For instance, for an initially positive-going pulse from zero, the change or transition from peak positive to peak negative will produce a strong contraction while for an initially negative-going pulse, the transition from peak negative to peak positive will produce a somewhat weaker contraction. This contractile imbalance, which typically causes discomfort, is balanced in the prior art by decreasing the width or the amplitude of the negative excursion of each pulse. Although this balances the contractile effect, there results an electrical imbalance with a resulting net ion flow which is disadvantageous for effective therapy.

It is also recognized that the pulse duration or width has an effect on the therapeutic effect as well as discomfort. Generally, the shorter the duration or width of the individual pulses the less of a contracting effect the pulse has on the muscle because the muscle has less time to respond to it. Generally, the therapeutic effect increases with pulse duration, up to a maximum duration of approximately 250 milliseconds. At the lower frequencies, the pulse energy is limited by limiting the pulse amplitude and/or pulse width to avoid irritation or damage to the tissue. Hence, the maximum therapeutic effect of low frequency is limited by the amount of muscle irritation and/or tissue damage which would be present.

FIG. 3 is a sine pulse diagram which illustrates a basic feature of the present invention. In FIG. 3, the polarity of successive pulses alternates, so that a given pulse 14 will comprise a positive excursion followed by a negative excursion, while the following pulse 15 comprises a negative excursion followed by a positive excursion. The next successive pulse 16 will have a similar polarity as the first pulse 14. The inventor has discovered that the result of this feature in a pulse train is a balanced muscle contraction without the corresponding effect of a net ion transfer and hence inherently reduced discomfort.

The contractile balance with no net ion flow is maintained even if certain other modifications to the pulse train, such as explained below, occur. Deeper penetration for the pulses is also possible (through the use of lower frequencies and longer pulse duration) since there are now two pulse rates in the pulse train, the original or primary pulse rate and a secondary subharmonic, as shown in FIG. 3. The primary pulse rate is established by the time between the leading edge of the negative excursion of successive pulses, while the secondary subharmonic is established by the time between the negative excursion of successive pulses having the same polarity, i.e. pulses 15 and 17 or pulses 14 and 16 in FIG. 3. A complete cycle at the primary pulse rate plus 50% of the cycle at the secondary pulse rate occurs before an inverted polarity match occurs. It has been demonstrated that the second frequency produces a deeper and more uniform penetration and contraction and results in the therapy being more comfortable.

Although FIG. 3 shows the alternating or mirroring of polarity for every other pulse, such alternating of polarity could occur at every third or fourth or any other pulse. However, the polarity change must occur consistently throughout the pulse train. Otherwise, some imbalance, either electrical or contractile, will occur.

Figure 15A:
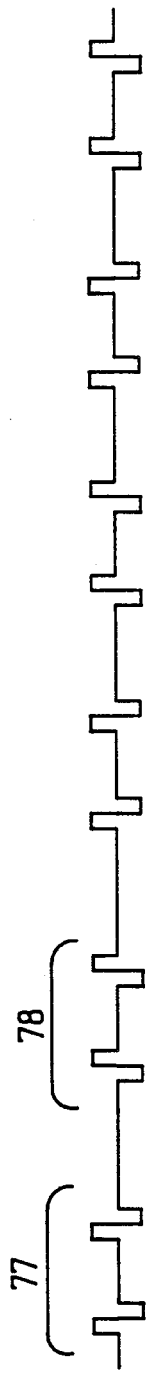
FIGS. 15A-15B are sine wave diagrams showing further features of the present invention, specifically the use of alternating pulse polarity for every other and every pulse, respectively.
Figure 15B:
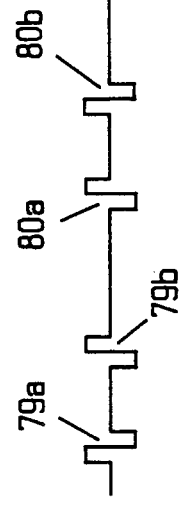

FIGS. 15A and 15B both also show a pulse balance using pulse inversion, but in a more complex pulse train using a four pulse grouping. FIG. 15A shows a phase inversion for each successive pair of pulses, i.e. the first pair of pulses 77 have initial positive excursions while the following pair of pulses 78 have initial negative excursions. FIG. 15B shows phase inversion for each pair of pulses. In the first pulse pair, pulse 79b is inverted relative to pulse 79a, which has an initial positive excursion, while in the second pulse pair, pulse 80b is inverted relative to pulse 80a, which has an initial negative excursion. Both of the pulse trains 15A and 15B have a slightly different contractile effect and are used for different purposes.

FIG. 4A shows a signal technique which tends to nullify the sensation of the subharmonic frequency shown in FIG. 3. The second half 18a of each pulse has a width which is less than the first half 18b. FIG. 4B shows a signal technique which tends to enhance the sensation or effect of the subharmonic frequency shown in FIG. 3. In this case, the second half 19a of each pulse has a width which is greater than the first half 19b.

FIG. 5 shows two more features which are helpful to reduce discomfort and which can be used either with the sine pulse train known in the art, or the sine pulse train produced by the apparatus of the present invention. One feature involves increasing the pulse width of one or both of the negative excursion 22 or the positive excursion 24 of pulse 25. Changing the pulse width of either or both of the positive and negative excursions, i.e. modulating the pulse width, on a defined basis at some specified fraction of the pulse rate results in a number of additional frequencies in the pulse train, which adds to the comfort of the treatment as well as increasing uniformity of the contractile effect and penetration of the pulses. As explained briefly above, each particular pulse rate and each particular pulse width has associated therewith a particular discomfort. Regular changing of the pulse rate and/or the pulse width has the effect of reducing the overall sense of discomfort since no one pulse rate and/or pulse width is maintained for long periods of time.

The other feature shown in FIG. 5 involves separating the negative excursion 21 from the positive excursion 23 of the same pulse, i.e. pulse 27, by some selected small interval of time 20. As long as the time separation remains fairly small, i.e. less than approximately 200 milliseconds, the combined positive and negative excursions will still look like a single pulse to the body. This time separation feature is referred to as null time.

Figure 7:
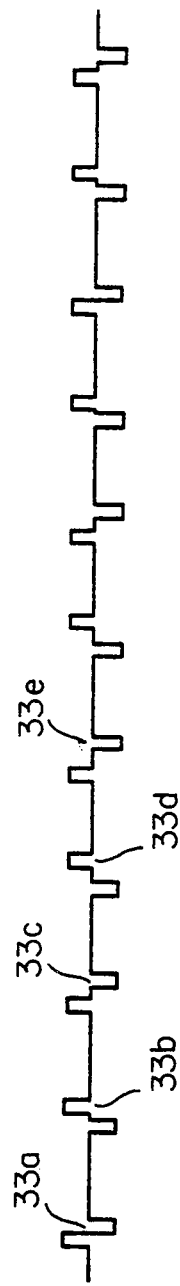
FIG. 7 is a sine pulse diagram similar to that of FIG. 6 and including the feature of null time modulation from zero null time.

The features shown in FIG. 5 also have been found to reduce the discomfort of pulses for a particular fixed frequency and pulse duration. Separation of the positive and negative excursions tends to further balance the contractile effect, i.e. the feel, of each pulse. The null time for successive pulses can be varied, i.e. modulated, on a regular basis, as shown in FIG. 6, which shows a null time for pulses 29a–29g which increases from 80 microseconds (29a) to 200 microseconds (29g), at which point it begins to decrease back to 80 microseconds. Varying the null time for successive pulses results in a continual gradual change in the contractile effect, so that one constant pulse shape does not become a source of irritation. FIG. 7 is similar to FIG. 6, but shows the modulation of null times for pulses 33a–33e where the null time begins from zero. In effect, the less the null time, the more the body tends to react to the peak-to-peak transition of the entire pulse, thereby modulating the contractile effect of each excursion portion of the pulse.

Figure 16:
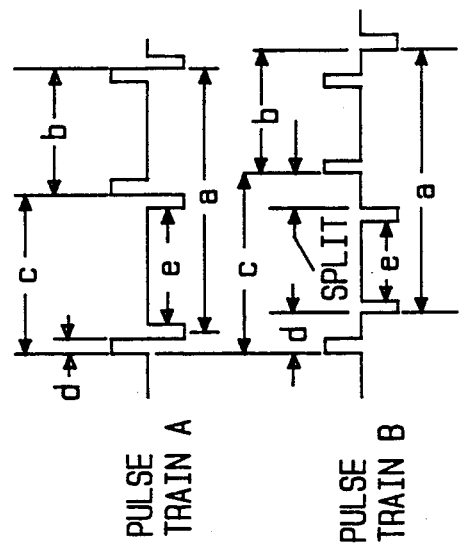
FIG. 16 is a sine wave diagram illustrating a still further feature of the present invention, specifically the use of null time to produce a multiple frequency effect.

FIG. 16 shows some of the detailed effects, in terms of subfrequencies, due to the time delay (null time) between the positive and negative excursion of the pulses, discussed above with respect to FIGS. 5, 6 and 7. FIG. 16 includes two pulse trains, one pulse train (A) having no time delays or split (null time) between the first and second excursions of each pulse, while the other (B) does have a time delay. Both pulse train A and pulse train B have the same primary frequency and one identical subharmonic frequency (frequencies a and b). Other frequencies, i.e. frequencies c, d (none in pulse train A) and e in each pulse train are different between the two pulse trains because of the time delay between the positive and negative excursions of each successive pulse of pulse train B. The frequencies c, d and e in pulse train B will vary with the length of the delay. Again, this feature provides significant flexibility and complexity for the overall pulse train, particularly when combined with the other features of the present invention discussed above.

FIG. 8 shows a sine pulse train incorporating the features of alternate pulse polarity inversion, as well as regular periodic changes in the pulse width. In particular, pulses 26 and 26a have a relatively wide pulse width while the succeeding two pulses 28 and 28a have a relatively narrow pulse width. This combination provides deep penetration at an acceptable comfort level. The pulses of FIG. 8 also include a very small null time, but this is not necessary.

The pulse train of FIG. 8 includes a primary pulse rate established by the time between the positive excursions of successive pulses having one selected pulse width. Second and third pulse rates are also created, with the second pulse rate established by the time between the leading edge of the first pulse in one pulse pair to the leading edge of the first pulse in the other pulse pair. The third pulse rate is established by the time between the leading edge of the first pulse of one pulse pair having a given width, to the leading edge of the first pulse in the next pulse pair having the same pulse width. Thus, pulse rates, i.e. frequencies, lower than the primary frequency can be conveniently introduced into a pulse train. As many subfrequencies as desired may be introduced. The subfrequencies may be either subharmonic in nature or they can be nonharmonic.

Figure 9:
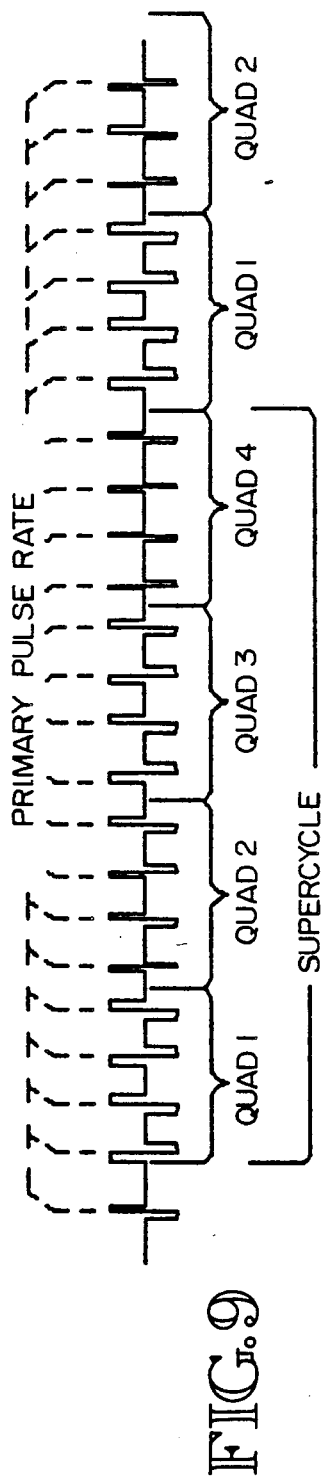
FIG. 9 is a sine pulse diagram illustrating another feature, referred to as a supercyle, of the present invention.

FIG. 9 shows a pulse train which includes a number of subharmonics, created by the use of pulse width modulation. In this pulse train, four successive sine pulses, with alternating polarity inversion, and with each pulse having a first pulse width, form a first group or "quad" of pulses. In the example of FIG. 9, there are four such quads, each with a different pulse width, such that the overall "supercycle" between identical pulses will cover a total of sixteen pulses and four quads. In this example, the primary frequency is 128 pulses per second, with major subharmonics of 64 pulses per second, 16 pulses per second and 8 pulses per second, with the 8 pulses per second being the frequency of the supercycle. Other nonharmonic frequencies are present in addition to these subharmonics. It should be understood that the primary frequency, and hence the subharmonics, could be readily changed, depending upon the particular therapeutic application.

Figure 10:
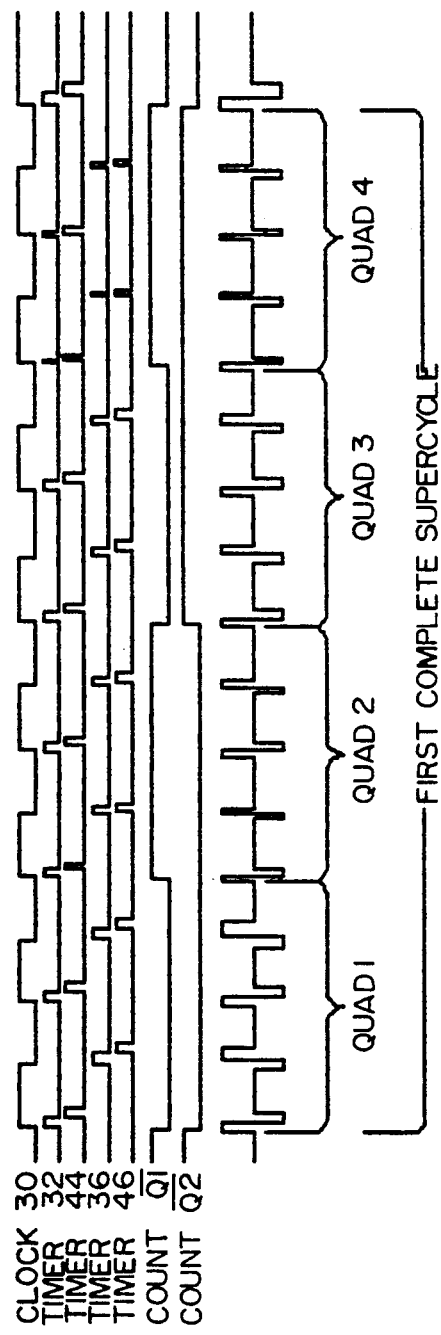
FIG. 10 is a particular sine pulse diagram illustrating several features of the present invention and the timing diagram to produce the sine pulse diagram.

FIGS. 10 and 11 show respectively the timing diagram and a circuit block diagram to produce the sine pulse train of FIG. 9 (also shown in FIG. 10). In FIG. 11, the clock circuit 30 produces a signal having a frequency between 2 and 64 pulses per second. The clock pulses are applied to a first timer 32, a binary counter 34, and through an inverter 31 to a second timer 36. The outputs of the first timer 32 and second timer 36 are applied to third and fourth timers 44 and 46, respectively. The outputs of the binary counter 34 on lines 38 and 40, at counts of four and eight clock pulses, respectively, are applied through inverting amplifiers 39 and 41 to a mix and match circuit 42, the output of which is fed back to change the pulse width of the outputs of first, second, third and fourth timers 32, 36, 44, 46 at selected time intervals.

The resulting pulses from the first through fourth timers 32, 36, 44, 46 are shown in the timing diagram of FIG. 10. The pulse output of timer 46 is applied to amplifier 48 for the positive excursion portion of the output pulses, along with the pulse output of the first timer 32. The pulse output of timer 44 is applied to amplifier 50 for the negative excursion portions of the output pulses, along with the pulse output from the second timer 36. The resulting outputs from the amplifiers 48 and 50 are then applied to a transformer 54, the output of which is shown as the signal train shown in FIG. 10.

FIGS. 12A–12D illustrate some of the basic general principles of another feature of the present invention, namely pulse pairing, showing how pulse pairing can be used to create subprimary and hyperprimary frequencies which are relatively close to the primary pulse rate, but still different enough to decrease the discomfort of a single pulse rate. The technique or feature of the present invention referred to as pulse pairing involves moving selected pulses in an original pulse train in time so as to produce new groupings of pulses. These groupings may be accomplished in pairs, pairs plus singles, triples, or others. The groupings should be such, however, as not to cause any ion or contractile imbalance in the pulse train as a whole. The result of pulse shifting to produce new groupings of pulses is to introduce even more subfrequencies into the overall pulse train, which increases the comfort of the pulse therapy, since there is no single frequency which would otherwise tend to become a source of discomfort.

FIG. 12A, specifically pulses 53a–53d, shows no pulse pairings, with a primary pulse rate of 48 pps, for example, and an additional harmonic of 24 pps. FIG. 12B shows one example of pulse pairing, with pulses 55a–55d resulting in frequencies of 48, 24, 64 and 38 pps, and the reduction of the effect of the primary frequency of 48 pps. In this example, alternate pulses, i.e. pulses 55b and 55d are shifted in time closer to alternate pulses 55a and 55c, respectively. Moving the pulse pairing closer, as shown in FIG. 12C, with pulses 57a–57d, produces frequencies of 48, 24, 77 and 35 pps, with the effect of the primary rate of 48 being further reduced. FIG. 12D, with pulses 59a–59d, produces frequencies of 48, 24, 96 and 32 pps. In this example, the effect of the primary frequency signal, 48 pps, is very small.

Figure 21:
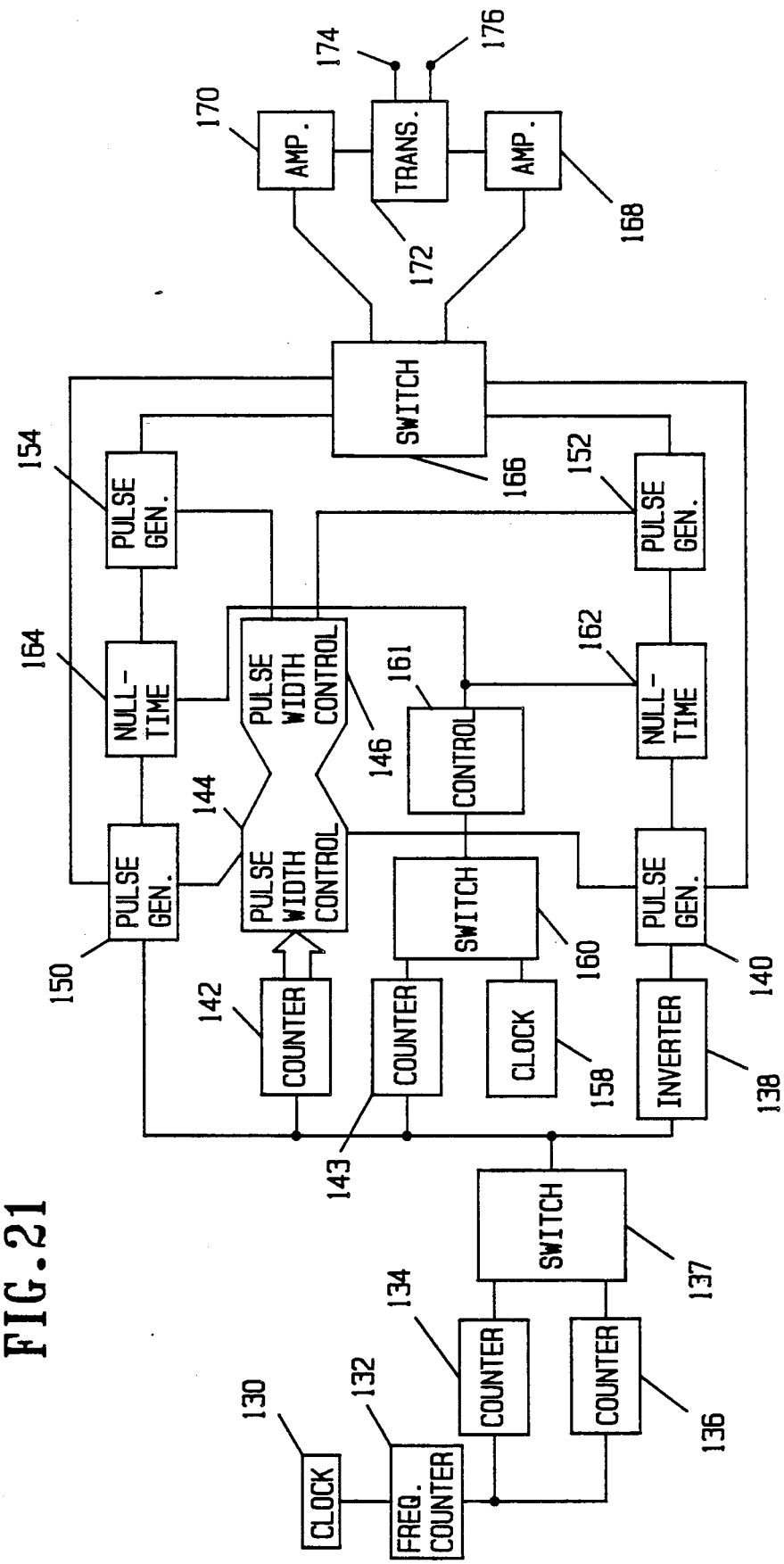
FIG. 21 is a circuit block diagram of an embodiment incorporating all of the features of the present invention.

FIG. 13 shows a sine pulse diagram for a further feature of the present invention, involving "swapping" or "pairing" of pulses at selected times along the pulse train, using a form of pulse modulation. In FIG. 13, the pulses are paired together by selectively modifying the ratio between the on and off times, respectively, of a clock (i.e. FIG. 11) or a counter such as shown in the circuit of FIG. 21. If the ratio of on/off time is directly inverted or reversed at regular intervals so that, for example, the ratio changes from 2 to 1 in favor of "on" time to 2 to 1 in favor of "off" time, the second pulse in a particular pulse pair in the train will leave its mate and shift to become the first pulse in a new pairing. Although this creates a slight imbalance of contractions, the continuous reversal at selected intervals will rebalance the overall effect.

If the pulse pairs are exchanged after an odd number of pulses, i.e. three, five, seven, each exchange will leave a single pulse in the sequence, while if the pulse pairs are exchanged after an even number of pulses, i.e. two or four, the sequence will alternate between leaving one pulse in between and three pulses in between.

Although a wide variety of pulse count combinations are possible with the structure shown in FIG. 11, generally 3, 4 and 5 pulse count shifts are preferred. FIG. 13, for instance, shows the pulse sequence for two full cycles using a 5 pulse shift. Pulse pairs 50 and 51 start and end with a positive excursion. The next pulse 52 is a single pulse, starting with a positive excursion. The following pulse pairs 54, 55 (after the switch or shift) start and end with a negative excursion, followed by a single pulse 56 which starts with a negative excursion. The group of pulses indicated at 58 illustrate the switching or pairing technique.

FIGS. 14A and 14B show two examples of pulse pairing using pairs and singles, with pulse inversion to achieve a complete balance, both ion and contractile. They each produce somewhat different therapeutic effects, however. FIG. 14A shows a 10 pulse grouping comprising two pairs of pulses 60–63 and a single pulse 64, which all begin with a positive excursion, while the following two pairs of pulses 67–70 and single pulse 71 begin with a negative excursion. FIG. 14B shows a similar balance for six pulses, i.e. pulse pair 72 and single pulse 73, each having initial positive excursions, followed by pulse pair 74 and single pulse 75, each having an initial negative excursion. Other similar balanced patterns may of course be created.

Combining the above-described techniques provides a wide range of therapeutic possibilities. Additional, simultaneous frequencies in the pulse train may be conveniently introduced into the pulse train, while maintaining an overall ion and contractile balance. Providing a null time between the two excursions of each pulse and in addition, modulating the null time will provide increased comfort capability. Groupings of pulses by ones, twos and threes, and combinations thereof provides a wide range of therapeutic possibilities.

FIGS. 17–21 show various embodiments for producing sine pulse trains having some or all of the features discussed above.

FIG. 17 is a circuit having a phase inversion capability. It includes a clock 81, an inverter 82, two pulse generators 84 and 86, associated amplifiers 88 and 90, and a transformer 92, which produces the pulse output. The center tap of the transformer is tied to the particular side of the power supply opposite in polarity to the pulse, i.e. if the pulses from amplifiers 88 and 90 are positive, the center tap is tied to the negative side of the power supply.

When the clock goes negative, the output at 94 goes first negative, then positive and when the clock goes positive, the output at 94 goes first positive, then negative. The opposite occurs for output 96. In the circuit of FIG. 17, however, matching transistors in amplifiers 88 and 90 are required.

FIG. 18 shows another circuit which does not require matching transistors. Clock 100 is connected to both an inverter 102 and a first pulse generator 104. The inverter is connected to a second pulse generator 106. The pulse generators 104 and 106 are connected to switches 108 and 110, respectively. The output of the switches are connected to a transformer 112, which has outputs 114 and 116. An amplifier 118 is connected to the center tap of the transformer 112. The switches 108 and 110 control the direction of the output pulses while the amplifier 118 controls the amplitude thereof.

Figure 19:
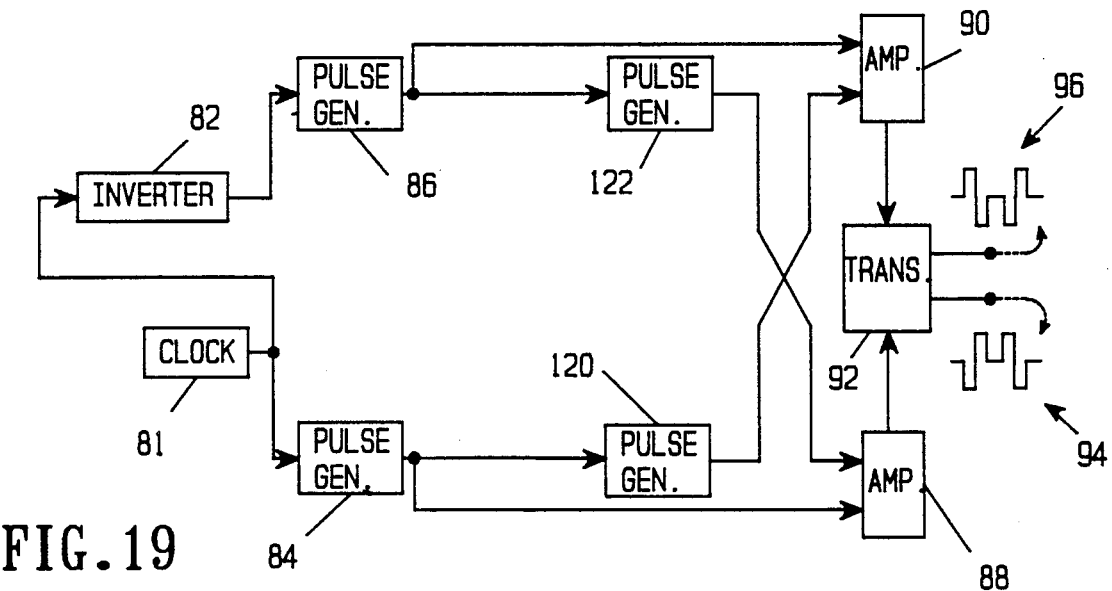
FIG. 19 is a circuit block diagram of an embodiment similar to that of FIG. 17, but incorporating an additional feature to provide more control over pulse shaping.

FIG. 19 shows the addition of two additional pulse generators 120, 122 to the circuit of FIG. 17. These generators are triggered by the negative transitions of the pulse output of the preceding respective pulse generators 84 and 86, respectively. As the pulse from generator 84 turns off amplifier 88, thus ending the negative excursion at output 94, it triggers pulse generator 120, which turns amplifier 90 on, producing a positive output at output 96. The opposite occurs for signal generators 86 and 122 when the clock goes from negative to positive. The output of this circuit produces a cleaner, more precise sine pulse having phase inversion than that shown in FIG. 17.

Figure 20:
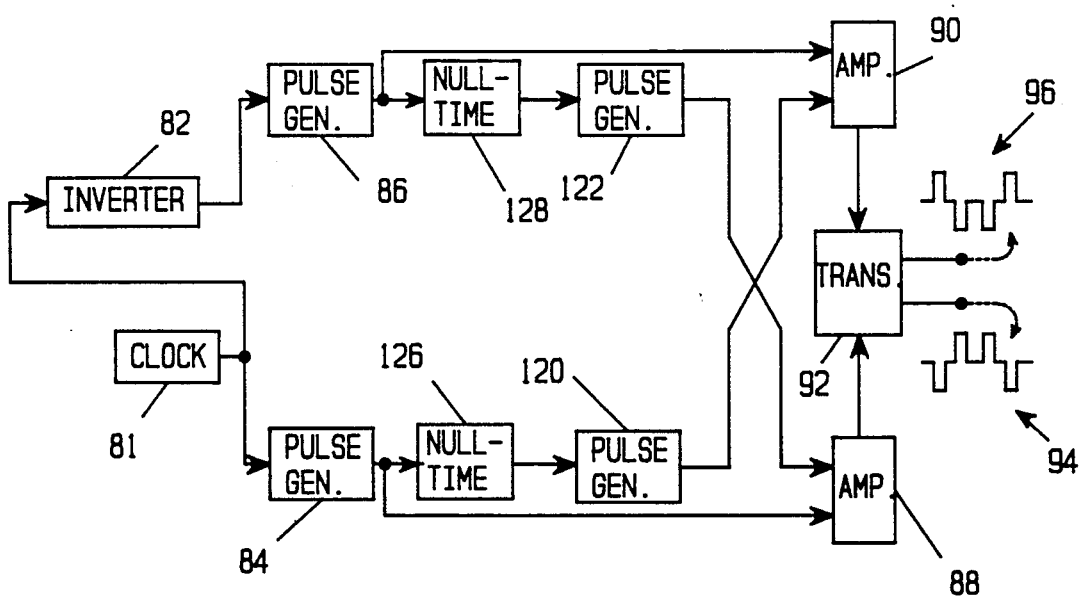
FIG. 20 is a circuit block diagram of an embodiment similar to that of FIG. 19, but incorporating an additional feature to provide null time control.

FIG. 20 includes two null-time generators 126, 128, positioned between the two pulse generators 84 and 120 and 86 and 122, respectively. The null-time generators produce a selected fixed delay between the two excursions of a single pulse at the output.

FIG. 21 shows a single circuit capable of producing a sine pulse train having all the possible variations and features discussed above. A clock 130 is connected to a pulse frequency counter 132, which is capable of dividing down the clock frequency. The output of the counter 132 is applied to a pulse grouping counter 134, which at a preselected count groups pulses into pairs, triples or pairs and singles. Also, the output of counter 132 is applied to a counter 136 which counts a preselected number of pulses without any grouping, i.e. a consistent, unchanging frequency. A switch 137 provides a capability of choosing between the two.

The switch 137 is connected to an inverter 138, as with the other circuits, which is connected to a first pulse generator 140. The output of switch 137 is also applied to counters 142 and 143. Counter 142 is used for pulse width modification, with circuits 144 and 146 controlling the width of the respective first and second excursions of the pulses. The output of pulse width control circuits 144 and 146 is applied to the pulse generators 140, 150, 152, and 154, for generation of the first and second excursions of the odd and even numbered sine pulses, respectively. Counter 143 is for null-time modification, as is clock 158. Hence, null time can be set at a specific amount, or it can be set to vary, either at a subharmonic rate relative to the clock 130 or independent of clock 130 through clock 158. Switch 160 controls the selection between the two. Circuit 161 controls the actual amount of null time, the output of which is applied to null time generators 162, 164.

Switch 166 provides the option of changing the output pulse shape and polarity. The output of switch 166 is applied to amplifiers 168, 170 which are in turn connected to transformer 172 which includes two output lines 174, 176.

The net result of the above disclosed sine pulse train features, including the capability of pulse modulation, results in a transcutaneous nerve/muscle stimulator apparatus which is capable of producing deep muscle/nerve penetration with high therapeutic value, without injury or irritation to the tissues or muscle itself. The circuits disclosed provide a wide capability of altering the pulse train in various respects and providing controlled modulation thereof. The present invention presents the possibility of significant improvements in therapy and pain control relative to prior art devices, as well as the possibility of relatively fast muscle development, all without significant discomfort.

Although a preferred embodiment of the invention has been disclosed herein for purposes of illustration, it should be understood that various changes, modifications and substitutions may be incorporated in such embodiment without departing from the spirit of the invention as defined by the claims which follow.

I claim:

1. An apparatus for transcutaneously stimulating nerves and/or muscles in a body, comprising:
   means for generating an electrical signal which includes a sequence of pulses having a selected basic pulse sequence frequency, wherein each pulse includes positive and negative excursions relative to a reference voltage;
   means for automatically changing the pulses in the pulse sequence between being initially positive-going and initially negative-going upon the successive occurrence of a predetermined number of pulses in the pulse sequence, thereby producing at least one harmonic frequency in the sequence of pulses in addition to the basic pulse sequence frequency; and
   electrode means attachable to the generating means for applying the electrical signal to the body.

2. An apparatus of claim 1, wherein said predetermined number of pulses is more than two.

3. An apparatus of claim 1, wherein said predetermined number of pulses is every other pulse.

4. An apparatus of claim 1, wherein the reference voltage is zero volts.

5. An apparatus of claim 1, including means for changing the amplitude of at least one of the positive and negative excursions of the pulses.

6. An apparatus of claim 1, including means for changing the time duration of at least one of the positive and negative excursions of the pulses.

7. An apparatus of claim 1, including means for varying the pulse width of the pulses.

8. An apparatus of claim 1, including means for separating the positive and negative excursions of each pulse with a selected time delay and means for varying said time delay.

9. An apparatus of claim 1, including means for modulating the amount of time delay such that the delay changes automatically in preselected increments at a predetermined rate between selected low and high values.

10. An apparatus of claim 1, including means for modulating the sequence of pulses to shift selected pulses in time within the pulse sequence.

11. An apparatus of claim 10, wherein the modulating means includes means for shifting the position of the pulses in the pulse sequence to produce selected groupings of pulses in the pulse sequence.

12. An apparatus for transcutaneously stimulating nerves and/or muscles in a body, comprising:
   means for generating an electrical signal which includes a sequence of pulses having a selected basic pulse sequence frequency, wherein each pulse includes positive and negative excursions relative to a reference voltage;
   means for automatically shifting individual pulses in time within the pulse sequence to form successive selected groupings of pulses, wherein the time between successive pulses in each pulse grouping is approximately the same, and is less than the time between successive pulse groupings; and
   electrode means attachable to the generating means for applying the electrical signal to the body.

13. An apparatus of claim 12, wherein the pulse groupings include groups of two pulses.

14. An apparatus of claim 12, wherein the pulse groupings includes groups of three pulses.

15. An apparatus of claim 12, including means for modulating the shifting of pulses so that the pulse groupings change automatically on a repetitive basis.

16. A method for transcutaneously stimulating nerves and/or muscles in a body, comprising the steps of:
   generating an electrical signal which includes a sequence of pulses having a selected basic pulse sequence frequency, wherein each pulse includes positive and negative excursions relative to a reference voltage;
   automatically changing the pulses between being initially positive going and initially negative going upon the successive occurrence of a predetermined number of pulses in the pulse sequence; and
   applying the electrical signal to the body.

17. A method of claim 16, including the step of changing the amplitude of at least one of the positive and negative excursions of the pulses.

18. A method of claim 16, including the step of changing the time duration of at least one of the positive and negative excursions of the pulses.

19. A method of claim 16, including the step of varying the pulse width of the pulses.

20. A method of claim 16, including the step of separating the positive and negative excursions of each pulse with a selected time delay.

21. A method of claim 20, including the step of modulating the amount of the time delay such that the delay changes automatically in preselected amounts at a predetermined rate between selected low and high values.

22. A method of claim 16, including the step of modulating the sequence of pulses to shift selected pulses in time within the pulse sequence.

23. A method of claim 22, including the step of shifting the position of the selected pulses in such a manner to produce selected groupings of pulses within the pulse sequence.

* * * * *

UNITED STATES PATENT AND TRADEMARK OFFICE
CERTIFICATE OF CORRECTION

PATENT NO. : 5,097,833
DATED : March 24, 1992
INVENTOR(S) : James M. Campos

It is certified that error appears in the above-identified patent and that said Letters Patent is hereby corrected as shown below:

In the claims, claim 9 should be dependent on claim 8, such that claim 9, line 1, should read as follows:

--An apparatus of claim 8, including means for mod- --.

Signed and Sealed this

Twenty-ninth Day of June, 1993

Attest:

*Attesting Officer*

MICHAEL K. KIRK

*Acting Commissioner of Patents and Trademarks*